US011291765B1

(12) United States Patent
Cheng et al.

(10) Patent No.: US 11,291,765 B1
(45) Date of Patent: Apr. 5, 2022

(54) SYRINGE PUMP

(71) Applicant: Lianying Medical Technology Co., Ltd., Hangzhou (CN)

(72) Inventors: Zhibiao Cheng, Lishui (CN); Jianguang Tu, Lishui (CN); Weihai Jiang, Lishui (CN)

(73) Assignee: Lianying Medical Technology Co., Ltd., Hangzhou (CN)

( * ) Notice: Subject to any disclaimer, the term of this patent is extended or adjusted under 35 U.S.C. 154(b) by 0 days.

(21) Appl. No.: 17/447,261

(22) Filed: Sep. 9, 2021

(30) Foreign Application Priority Data

Sep. 24, 2020 (CN) .......................... 202011014998.2

(51) Int. Cl.
*A61M 5/145* (2006.01)
*A61M 5/315* (2006.01)

(52) U.S. Cl.
CPC ........ *A61M 5/1454* (2013.01); *A61M 5/3153* (2013.01); *A61M 5/31505* (2013.01);
(Continued)

(58) Field of Classification Search
CPC ............ A61M 5/1454; A61M 5/31505; A61M 5/31511; A61M 5/3153; A61M 2205/18;
(Continued)

(56) References Cited

U.S. PATENT DOCUMENTS 5,295,967 A * 3/1994 Rondelet ........... A61M 5/16854
128/DIG. 12
9,399,096 B2 7/2016 Keenan et al.
(Continued)

FOREIGN PATENT DOCUMENTS

CN    101856528 A    10/2010
CN    203710476 U    7/2014
(Continued)

OTHER PUBLICATIONS

"Chinese Application No. 202011014998.2, Decision to Grant a Patent dated Apr. 30, 2021", (dated Apr. 30, 2021), 3 pgs.
(Continued)

*Primary Examiner* — Bradley J Osinski
(74) *Attorney, Agent, or Firm* — Schwegman Lundberg & Woessner, P.A.

(57) ABSTRACT

The disclosure relates to a control method of a syringe pump, a syringe pump and a computer-readable storage medium. In the control method of the syringe pump, by determining whether a pressure of the first pressure sensor is less than a first pressure threshold and actively stopping an injection process when the pressure of the first pressure sensor is greater than or equal to the pressure threshold, it can be achieved to accurately determine whether a subject can bear an injection pressure, and to actively stop the injection and sound an alarm when a pressure in the infusion tube exceeds a bearing limit of the subject, thus ensuring personal safety of the subject. When the pressure of the first pressure sensor is less than the first pressure threshold, it is further determined whether a pressure of the second pressure sensor with higher sensitivity is less than a second pressure threshold, and when the pressure of the second pressure sensor is greater than or equal to the pressure threshold, the injection process can be actively stopped and an alarm can be sounded, thus realizing dual monitoring of the pressure in the infusion tube.

5 Claims, 4 Drawing Sheets

(52) U.S. Cl.
   CPC ..... *A61M 5/31511* (2013.01); *A61M 2205/18* (2013.01); *A61M 2205/3331* (2013.01)

(58) Field of Classification Search
   CPC .. A61M 2205/3331; A61M 2205/3344; A61M 2005/16863
   See application file for complete search history.

(56) References Cited

U.S. PATENT DOCUMENTS

| | | | | |
|---|---|---|---|---|
| 2004/0057855 | A1* | 3/2004 | Gerlach | A61M 5/142 417/469 |
| 2012/0283691 | A1* | 11/2012 | Barnes | A61M 5/16854 604/500 |
| 2013/0030290 | A1 | 1/2013 | Nemoto | |

FOREIGN PATENT DOCUMENTS

| | | |
|---|---|---|
| CN | 105188796 A | 12/2015 |
| CN | 210992261 U | 7/2020 |
| WO | WO-2009152322 A2 | 12/2009 |
| WO | WO-2014100658 A1 | 6/2014 |

OTHER PUBLICATIONS

"Chinese Application No. 202011014998.2, First Office Action dated Jan. 18, 21", (dated Jan. 18, 2021), 7 pgs.

"Chinese Application No. 202011014998.2, Search Report dated Jan. 12, 2021", (dated Jan. 12, 2021), 2 pgs.

"Chinese Application No. 202011014998.2, Second Office Action dated Feb. 26, 21", (dated Feb. 26, 2021), 8 pgs.

* cited by examiner

SYRINGE PUMP

CROSS-REFERENCE TO RELATED APPLICATIONS

This Non-provisional application claims priority under 35 U.S.C. § 119(a) to Chinese Patent Application No. 202011014998.2, filed on 24 Sep. 2020, the entire contents of which are hereby incorporated by reference in its entirety.

TECHNICAL FIELD

The disclosure relates to a technical field of a syringe pump, in particular to a syringe pump.

BACKGROUND ART

A syringe pump is commonly used in an administration procedure in clinical treatment, which can control an infusion speed by acting on an infusion catheter. The syringe pump is commonly used in an infusion situation in which a strict control of infusion volume and dosage is required, for example, when applying a pressor drug and an antiarrhythmic drug to a patient, or applying intravenous infusion or intravenous anesthesia to an infant.

The infusion speed of an infusion pump is different depending on nature of a drug and physical fitness of a patient. A too fast or too slow infusion can hardly achieve a desired therapeutic effect, and even affect life safety of patients.

In a traditional syringe pump and control method of a syringe pump, when liquid medicine is injected, generally, medical personnel actively view a display screen of the syringe pump to know a current injection speed and pressure of the syringe pump.

The traditional syringe pump and the control method of the syringe pump have a problem that it is not accurate to determine whether the patient can bear the injection pressure. A displayed value of the display screen of the syringe pump may not be completely accurate, which poses a potential safety hazard during administration of the syringe pump.

SUMMARY

Therefore, in view of a problem that it cannot accurately be determined whether a patient can bear an injection pressure of a syringe pump in a control method of a traditional syringe pump and the syringe pump, it is necessary to provide a syringe pump.

The disclosure provides a syringe pump comprising:

a housing, a first surface of which is concave and a second surface of which is provided with a through hole;

a driving device provided inside the housing to drive a push handle seat to move;

a processor provided inside the housing to send control orders to drive a push handle seat to move;

a display device movably connected with the first surface, the display device being configured to be foldable so that when the display device is folded in a direction close to the first surface, the display device can be covered on the first surface to form an accommodation space with the first surface;

a syringe provided in the accommodation space, the syringe including a barrel and a ram;

a syringe clip fixedly provided on the first surface for clamping and fixing the syringe;

a push handle seat provided with a syringe snap which is configured for snapping the syringe on the push handle seat;

a connecting rod, one end of which extends into the through hole and is connected with the driving device, and the other end of which extends out of the through hole and is connected with the push handle seat;

an infusion tube, one end of which is connected with the barrel and the other end of which is connected with a puncture needle;

a first pressure sensor fixedly provided on the push handle seat; and a second pressure sensor attached to the first surface of the membrane piece for detecting a pressure in the infusion tube; and an alarm device provided inside the housing and electrically connected with the processor; wherein the processer implemented for acquiring the pressure value of the first pressure sensor in real time, determining whether the pressure value of the first pressure sensor is smaller than the first pressure threshold; and controlling the driving device to stop driving the push handle seat to move if the pressure value of the first pressure sensor is greater than or equal to the first pressure threshold;

the processer is further implemented for acquiring the pressure value of the second pressure sensor if the pressure value of the first pressure sensor has been determined to be smaller than the first pressure threshold, determining whether the pressure value of the second pressure sensor is smaller than the second pressure threshold; and controlling the driving device to stop driving the push handle seat to move if the pressure value of the second pressure sensor is greater than or equal to the second pressure threshold.

Further, the first surface is provided with a groove, the infusion tube includes a first tube and a second tube, and the syringe pump further includes:

a pressure detection module embedded in the groove;

the pressure detection module including:

a membrane piece including a first surface of the membrane piece and a second surface of the membrane piece, a flexible membrane being provided on the first surface of the membrane piece and the flexible membrane being recessed in a direction close to the second surface of the membrane piece; and one end of the first tube being connected with the puncture needle, and the other end of the first tube being connected with the membrane piece; and one end of the second tube being connected with the membrane piece, and the other end of the second tube being to connected with the barrel.

Further, the pressure detection module further includes:

a pressure conducting block provided between the second pressure sensor and the membrane piece and attached to the flexible membrane.

Further, the pressure detection module further includes a spring and a pressure support block.

The pressure support block is arranged between the spring and the membrane piece and is attached to the second surface of the membrane piece.

At least one bump is provided on a surface of the pressure support block, and at least one pocket is provided on the second surface of the membrane piece. The bump and the pocket are arranged to be matched with each other, so that the pressure support block and the membrane piece are closely attached.

Further, sensitivity of the second pressure sensor is greater than that of the first pressure sensor.

The disclosure also provides a computer-readable storage medium including a computer program, which, when executed on a syringe pump, causes the syringe pump to execute the control method of the syringe pump described above.

The disclosure relates to a control method of a syringe pump, a syringe pump and a computer-readable storage medium, in which a real-time detection of the pressure in the infusion tube during an injection process is realized, by acquiring the pressure of the first pressure sensor and the pressure of the second pressure sensor in real time during the injection process. By determining whether the pressure of the first pressure sensor is less than the first pressure threshold and actively stopping the injection process when the pressure of the first pressure sensor is greater than or equal to the pressure threshold, it can be achieved to accurately determine whether the subject can bear an injection pressure, and to actively stop the injection and sound an alarm when the pressure in the infusion tube exceeds a bearing limit of the subject, thus ensuring personal safety of the subject.

In addition, when the pressure of the first pressure sensor is less than the first pressure threshold, it is further determined whether the pressure of the second pressure sensor with higher sensitivity is less than the second pressure threshold, and when the pressure of the second pressure sensor is greater than or equal to the pressure threshold, the injection process can be actively stopped and an alarm can be sounded, thus realizing dual monitoring of the pressure in the infusion tube.

REFERENCE NUMBER

10—Housing; 110—First Surface; 111—Groove; 120—Second Surface; 121—Through Hole;
20—Driving Device; 210—Push Handle Seat; 211—Syringe Snap; 220—Connecting Rod; 30—Processor;
40—Display Device; 50—Syringe; 510—Barrel; 520—Ram; 60—Syringe Clip;
530—Infusion Tube; 531—First Tube; 532—Second Tube; 540—Puncture Needle;
710—First Pressure Sensor; 720—Second Pressure Sensor; 80—Pressure Detection Module;
810—Membrane Piece; 811—First Surface of Membrane Piece;
812—Second Surface of Membrane Piece; 813—Flexible Membrane;
820—Pressure Conducting Block; 830—Pressure Support Block; 840—Spring; 851—Upper Protective Housing;
852—Lower Protective Housing; 90—Alam Device

DETAILED DESCRIPTION

In order to make the objects, technical schemes and advantages of the present disclosure more clear, the present disclosure will be further described in detail with reference to the drawings and examples. It should be understood that the specific embodiments described herein are only used to explain the present disclosure, and are not intended to limit the present disclosure.

The disclosure provides a control method of a syringe pump. It should be noted that the control method of the syringe pump provided in this disclosure is applicable to any type of syringe pump. Optionally, the control method of the syringe pump provided by the disclosure is suitable for the syringe pump used for critically ill patients.

In addition, the control method of the syringe pump provided by the disclosure is not limited in its executing body. Optionally, the executing body of the control method of the syringe pump provided in the disclosure can be a syringe pump. Specifically, the executing body of the control method of the syringe pump provided in this disclosure can be one or more processors 30 in the syringe pump.

Figure 1:
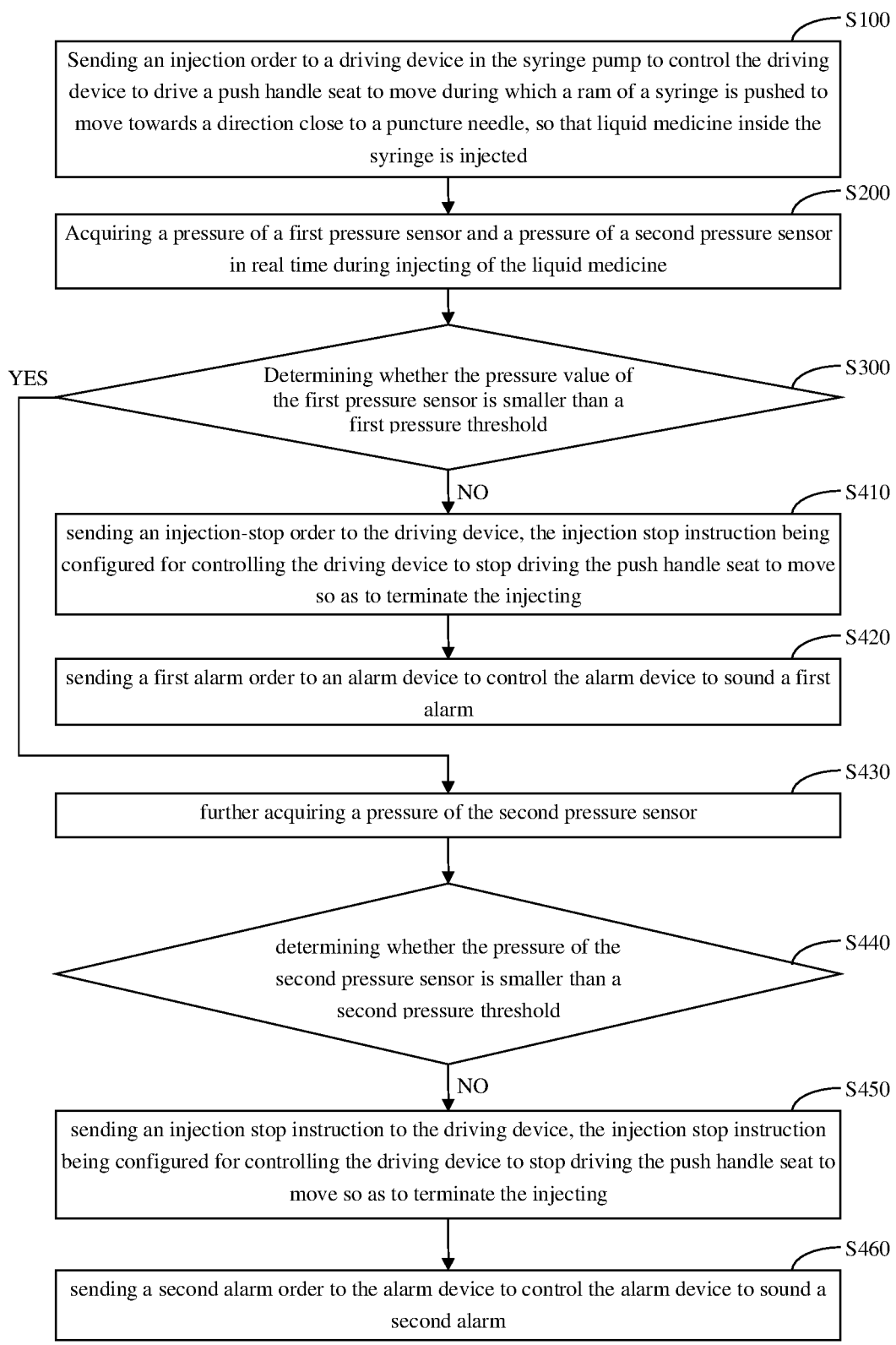
FIG. 1 is a schematic flow chart of a control method of a syringe pump according to an embodiment of the present disclosure.

As shown in FIG. 1, in an embodiment of the present disclosure, a control method of a syringe pump includes following steps S100 to S460.

In S100, an injection order is sent to a driving device 20 in the syringe pump to control the driving device 20 to drive the push handle seat 210 to move. During the moving of the push handle seat 210, a ram 520 of a syringe 50 is pushed to move towards a direction close to a puncture needle 540, so that liquid medicine inside the syringe 50 is injected into a blood vessel of a subject.

Specifically, this step is a process of injecting the liquid medicine inside the syringe 50. The processor 30 sends an injection order to the driving device 20, and the driving device 20 drives the push handle seat 210 to move, so that this step is executed.

In S200, during injecting of the liquid medicine, pressures of a first pressure sensor 710 and a second pressure sensor 720 are acquired in real time. The first pressure sensor 710 is provided in the push handle seat 210 of the syringe pump. The second pressure sensor 720 is attached to the infusion tube 530 between the puncture needle 540 and the syringe 50.

Specifically, during the injecting, the first pressure sensor 710 acquires a pressure in the infusion tube in real time and feeds it back to the processor 30 in real time. Further, the processor 30 acquires the pressure sent by the first pressure sensor 710 in real time.

The second pressure sensor 720 acquires the pressure in the infusion tube in real time and feeds it back to the processor 30 in real time. A difference between the pressure in the infusion tube acquired by the second pressure sensor 720 and the pressure in the infusion tube acquired by the first pressure sensor 710 is that sensitivity of the second pressure sensor 720 is high and the pressure in the infusion tube acquired by the second pressure sensor 720 is the one affected by a blood pressure of a subject. Further, the processor 30 acquires the pressure of the second pressure sensor 710 in real time.

In S300, it is determined whether the pressure of the first pressure sensor 710 is smaller than a first pressure threshold.

Specifically, the first pressure threshold is the one preset with multiple tests of the syringe pump before production combined with literature data. By comparing the pressure of the first pressure sensor 710 with the first pressure threshold, it can be known whether a current pressure in the infusion tube reaches a relatively high level.

In S410, an injection-stop order is sent to the driving device 20 if the pressure of the first pressure sensor 710 is greater than or equal to the first pressure threshold. The injection-stop order is configured for controlling the driving device 20 to stop driving the push handle seat 210 to move so as to terminate the injecting.

Specifically, if the pressure of the first pressure sensor 710 is greater than or equal to the pressure threshold, it indicates that the current pressure in the infusion tube has reached the relatively high level, and the subject cannot bear the pressure in the infusion tube. If the injection goes on, the subject will be subjected to life-threatening phenomenon such as blood vessel rupture. At this time, the processor 30 controls the driving device 20 to stop driving the push handle seat 210 to move so as to terminate the injecting.

In S420, a first alarm order is sent to an alarm device 90 to control the alarm device 90 to sound a first alarm.

Specifically, at this time, the processor 30 not only controls the driving device 20 to stop driving the push handle seat 210 to move so as to terminate the injecting, but also controls the alarm device 90 to sound the first alarm to alert medical staff.

In S430, a pressure of the second pressure sensor 720 is further acquired if the pressure of the first pressure sensor 710 is less than the first pressure threshold.

Specifically, if the pressure of the first pressure sensor 710 is less than the pressure threshold, it cannot be determined the current pressure in the infusion tube is safe, and it is necessary to further acquire the pressure of the second pressure sensor 720. Optionally, the sensitivity of the second pressure sensor 720 is higher than that of the first pressure sensor 710, so it is more accurate to determine a pressure the subject bears according to the pressure of the second pressure sensor 720.

In S440, it is determined whether the pressure of the second pressure sensor 720 is smaller than a second pressure threshold.

Specifically, the second pressure threshold is smaller than the first pressure threshold.

In S450, an injection-stop order is sent to the driving device 20 if the pressure of the second pressure sensor 720 is greater than or equal to the second pressure threshold. The injection-stop order is configured for controlling the driving device 20 to stop driving the push handle seat 210 to move so as to terminate the injecting.

Specifically, the sensitivity of the second pressure sensor 720 is higher. It is further determined whether the pressure of the second pressure sensor 720 with the higher sensitivity is less than the second pressure threshold, and when the pressure of the second pressure sensor 720 is greater than or equal to the pressure threshold, the injection process can be actively stopped and an alarm can be sounded, thus realizing dual monitoring of the pressure in the infusion tube.

On the contrary, if the pressure of the second pressure sensor 720 is less than the second pressure threshold, it indicates that the subject can bear the pressure in the infusion tube, and then the control method returns to step S200 to continuously monitor the pressures of the first pressure sensor 710 and the second pressure sensor 720.

In S460, a second alarm order is sent to the alarm device 90 to control the alarm device to sound a second alarm.

Specifically, a tone color of the second alarm sound is different from that of the first alarm sound.

In this embodiment, a real-time detection of the pressure in the infusion tube during an injection process is realized, by acquiring the pressure of the first pressure sensor 710 and the pressure of the second pressure sensor 720 in real time during the injection process. By determining whether the pressure of the first pressure sensor 710 is less than the first pressure threshold and actively stopping the injection process when the pressure of the first pressure sensor 710 is greater than or equal to the pressure threshold, it can be achieved to accurately determine whether the subject can bear an injection pressure, and to actively stop the injection and sound an alarm when the pressure in the infusion tube exceeds a bearing limit of the subject, thus ensuring personal safety of the subject.

When the pressure of the first pressure sensor 710 is less than the first pressure threshold, it is further determined whether the pressure of the second pressure sensor 720 with higher sensitivity is less than the second pressure threshold, and when the pressure of the second pressure sensor 720 is greater than or equal to the pressure threshold, the injection process can be actively stopped and an alarm can be sounded, thus realizing dual monitoring of the pressure in the infusion tube.

In an embodiment of the present disclosure, before the step S100, the control method of the syringe pump further includes following steps S010 to S020.

In S010, the pressure in the infusion tube affected by the blood pressure of the subject is acquired by the second pressure sensor 720 when the puncture needle 540 penetrates into the blood vessel of the subject.

Specifically, one end of the infusion tube 530 is connected with the puncture needle 540, and the other end of the infusion tube is connected with the barrel 510 of the syringe 50. The push handle seat 210 is connected with the syringe 50, and the push handle seat 210 is used for pushing the ram 520 of the syringe 50 to move.

When the syringe pump starts to work, the puncture needle 540 penetrates into the blood vessel of the subject. At this time, the second pressure sensor 720 can acquire the pressure in the infusion tube. At this time, the pressure in the infusion tube is affected by the blood pressure of the subject, and change in the affected pressure and its specific value are determined according to physiological quality of the subject.

Further, the second pressure sensor 720 sends the acquired pressure in the infusion tube affected by the blood pressure of the subject to the processor 30.

S020, calculating a second pressure threshold according to the pressure in the infusion tube affected by the blood pressure of the subject.

Specifically, this step is intended to calculate the second pressure threshold, that is, to calculate the injection pressure that the subject can bear. A type of algorithm invoked by the processor 30 to calculate the second pressure threshold is not limited.

Optionally, this step can be performed after the puncture needle 540 penetrates into the blood vessel of the subject and the syringe pump is started for 3 to 5 seconds. This is because when the syringe pump is just started, there is a certain fluctuation effect on the pressure in the infusion tube, which affects acquisition results of the pressure in the infusion tube affected by the blood pressure of the subject, and further affects accuracy of a calculation result of the second pressure threshold.

The calculation result is more accurate after the syringe pump is started for 3 to 5 seconds before executing a calculation of the second pressure threshold in step S020.

In this embodiment, the pressure in the infusion tube affected by the blood pressure of the subject is acquired by the second pressure sensor 720 and the second pressure threshold is calculated according to the pressure in the infusion tube affected by the blood pressure of the subject, thus realizing the accurate and real-time calculation of the injection pressure that the subject can bear before injecting the liquid medicine.

In an embodiment of the present disclosure, before the step S100, the control method of the syringe pump further includes a following step S030.

In S030, a pressure fluctuation in the infusion tube affected by the blood pressure of the subject is acquired by the second pressure sensor 720.

Specifically, for some subjects with weak blood vessels, such as children, it is not enough to monitor whether the pressure in the infusion tube reaches the pressure threshold by only acquiring the pressure in the infusion tube in real time by the first pressure sensor 710 and the second pressure sensor 720. it is necessary to synchronously acquire the pressure fluctuation in the infusion tube affected by the subject by the second pressure sensor 720 provided in this embodiment, while step S200 is executed.

Optionally, the sensitivity of the second pressure sensor 720 is far greater than that of the first pressure sensor 710, and can detect the pressure fluctuation in the infusion tube in real time. The second pressure sensor 720 is disposed between the puncture needle 540 and the barrel 510 of the syringe 50.

In this way, not only the pressure in the infusion tube affected by the blood pressure of the subject can be acquired in real time, but also the pressure fluctuation in the infusion tube affected by the subject can be acquired. In other words, both its specific value and a fluctuation range of the specific value are known.

In this embodiment, with the second pressure sensor 720 provided to acquire the pressure fluctuation in the infusion tube affected by the subject, the pressure fluctuation situation in the infusion tube can be acquired in real time.

In an embodiment of the present disclosure, the step S200 further includes following step S210.

In S210, the pressure fluctuation of the second pressure sensor 720 is acquired in real time during the injecting of the liquid medicine.

Specifically, during the injecting of the liquid medicine, the second pressure sensor 720 can acquire the fluctuation of the pressure in the infusion tube in real time and feed it back to the processor 30.

In this embodiment, the processor 30 acquires the pressure fluctuation of the second pressure sensor 720 in real time, so that the processor 30 can acquire the pressure fluctuation in the infusion tube in real time.

In an embodiment of the present disclosure, the control method of the syringe pump further includes following steps S470 to S490.

In S470, it is further determined whether a pressure fluctuation of the second pressure sensor 720 is less than the pressure fluctuation in the infusion tube affected by the subject if the pressure of the second pressure sensor 720 is less than the second pressure threshold.

In S480, an injection-stop order is sent to the driving device 20 if the pressure fluctuation of the second pressure sensor 720 is greater than or equal to the pressure fluctuation in the infusion tube affected by the subject. The injection-stop order is configured for controlling the driving device 20 to stop driving the push handle seat 210 to move so as to terminate the injecting.

In S490, a third alarm order is sent to an alarm device 90 to control the alarm device 90 to sound a third alarm.

Specifically, in the aforementioned embodiment, if the pressure of the second pressure sensor 720 is less than the second pressure threshold, it indicates that the subject can bear the pressure in the infusion tube, and then the control method returns to step S200 to continuously monitor the pressures of the first pressure sensor 710 and the second pressure sensor 720. However, in this embodiment, when the pressure of the second pressure sensor 720 is less than the second pressure threshold, although a specific value of the pressure in the infusion tube does not exceed the second pressure threshold, it still cannot be determined whether the subject can bear the pressure in the infusion tube, and it is necessary to further determine whether the pressure fluctuation in the infusion tube exceeds the pressure fluctuation affected by the subject acquired in step S210.

If the pressure fluctuation of the second pressure sensor 720 is greater than or equal to the pressure fluctuation in the infusion tube affected by the subject, it indicates that the subject cannot bear the current pressure fluctuation in the infusion tube, which can be understood as that the subject cannot bear such drastic pressure change, so the processor 30 sends an injection-stop order to the driving device 20, and controls the driving device 20 to stop driving the push handle seat 210 to move to terminate the injecting.

In addition, the processor 30 also controls the alarm device 90 to sound a third alarm.

If the pressure fluctuation of the second pressure sensor 720 is less than the pressure fluctuation in the infusion tube affected by the subject, it indicates that the subject can bear both the current pressure in the infusion tube and the current pressure fluctuation in the infusion tube, and the subject is safe, and then the control method returns to step S200 to continuously monitor the pressures of the first pressure sensor 710 and the second pressure sensor 720.

In this embodiment, after determining that the subject can bear the pressure in the infusion tube, it is further determined whether the subject can bear the pressure fluctuation in the infusion tube, so that the injection is actively stopped when the pressure fluctuation in the infusion tube exceeds a bearing limit of the subject, and personal safety of the subject is guaranteed.

In an embodiment of the disclosure, the control method of the syringe pump further includes a following step S500.

In S500, the retreating order is sent to the driving device 20 to control the driving device 20 to drive the push handle seat 210 to move during which the ram 520 of the syringe 50 is pulled to move towards a direction away from the puncture needle 540.

Specifically, after step S420, step S500 is executed. After step S460, step S500 is also executed. In other words, the step S500 is executed after the injection is terminated and an alarm is sounded.

In this embodiment, the processor 30 not only controls the driving device 20 to stop driving the push handle seat 210 to stop the injection, but also controls the push handle seat 210 to retreat and pull the ram 520 of the syringe 50 to move towards a direction away from the puncture needle 540. A purpose of this step is to reduce the pressure in the infusion tube, relieve discomfort of the subject and get the subject out of danger in time.

It should be noted that, during the operation, the moving of the push handle seat 210 is not obvious to the naked eye, and it is a slight movement.

In this embodiment, when the pressure of the first pressure sensor 710 is greater than or equal to the first pressure threshold, or when the pressure of the second pressure sensor 720 is greater than or equal to the second pressure threshold, with a retreating order being sent to the driving device 20, the push handle seat 210 can pull the ram 520 to retreat, which can effectively reduce the pressure in the infusion tube, relieve the discomfort of the subject, and help the subject get rid of a dangerous state in time.

In an embodiment of the present disclosure, the step S500 includes following steps S510 to S540.

In S510, the retreating order is sent to the driving device 20 to control the driving device 20 to drive the push handle seat 210 to move. During moving, the push handle seat 210 pulls the ram 520 of the syringe 50 to move towards the direction away from the puncture needle 540.

In S520, the pressure of the second pressure sensor 720 is acquired in real time during the moving of the ram 520.

In S530, it is determined whether the pressure of the second pressure sensor 720 is smaller than a second pressure threshold.

In S540, the retreating-stop order is sent to the driving device 20 if the pressure of the second pressure sensor 720 is smaller than the second pressure threshold. The retreating-stop order is configured for controlling the driving device 20 to stop driving the push handle seat 210 to move so as to terminate the moving of the ram 520.

Specifically, it can be understood that when the ram 520 of the syringe 50 retreats, a small amount of blood enters the infusion tube 530 due to the retracting. Although a purpose of the retreating is to reduce the pressure in the infusion tube, the retreating is limited so that an excessive blood loss of the subject is not caused.

This embodiment shows such a closed-loop control logic.

Since the sensitivity of the second pressure sensor 720 is far greater than that of the first pressure sensor 710, it is more accurate to read the pressure of the second pressure sensor 720 directly without reading the pressure of the first pressure sensor 720. It is determined whether the pressure of the second pressure sensor 720 is smaller than the second pressure threshold. If the second pressure sensor 720 has sensed a significant pressure drop and dropped below the second pressure threshold, it is not necessary to reduce the pressure at this time, and the retreating-stop order is immediately sent to the driving device 20 to prevent the subject from losing too much blood.

Since the second pressure threshold is smaller than the first pressure threshold, if the pressure of the second pressure sensor 720 is smaller than the second pressure threshold, the pressure of the second pressure sensor 720 must also be smaller than the first pressure threshold, so the first pressure threshold is compared.

In this embodiment, by determining whether the pressure of the second pressure sensor 720 is less than the second pressure threshold, and sending the retreating-stop order to the driving device 20 in time when the pressure of the second pressure sensor 720 is less than the second pressure threshold, the subject can be prevented from losing too much blood.

In an embodiment of the present disclosure, after the step S530, the step S500 further includes step S550.

In S550, the ram 520 is continuously moved and the control method returns to step S520 if the pressure of the second pressure sensor 720 is greater than or equal to the second pressure threshold.

Specifically, in this step, if the pressure of the second pressure sensor 720 is greater than or equal to the second pressure threshold, and the pressure in the surface infusion tube has not dropped, the ram 520 is continuously moved and the control method returns to step S520 to continuously monitor the pressure of the second pressure sensor 820.

The disclosure also provides a syringe pump. The syringe pump is configured for executing the control method of the syringe pump described in any of the previous embodiments.

Figure 2:
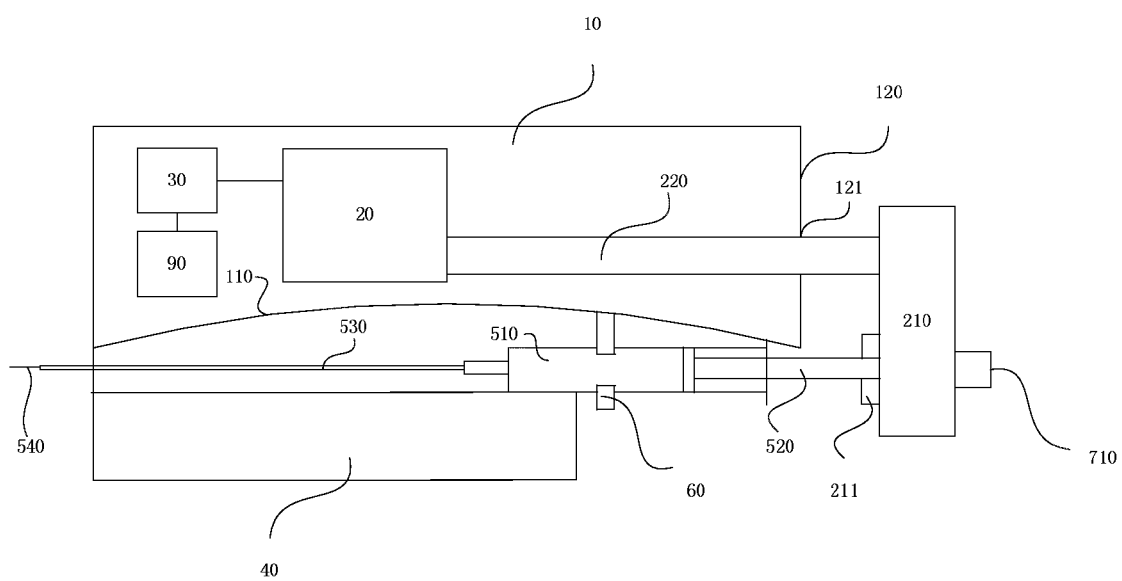
FIG. 2 is a schematic structural diagram of a syringe pump according to an embodiment of the present disclosure.

As shown in FIG. 2, in an embodiment of the present disclosure, the syringe pump includes a housing 10, a driving device 20, a processor 30, a display device 40, a syringe 50, a syringe clip 60, a push handle seat 210, a connecting rod 220, an infusion tube 530, a first pressure sensor 710 and an alarm device 90.

A first surface 110 of the housing 10 is concave. A second surface 120 of the housing 10 is provided with a through hole 121. The driving device 20 is provided inside the housing 10. The processor 30 is provided inside the housing 10. The display device 40 is movably connected with the first surface 110. The display device 40 is configured to be foldable. When the display device 40 is folded in a direction close to the first surface 110, the display device can be covered on the first surface 110 to form an accommodation space with the first surface 110.

The syringe 50 is provided in the accommodation space. The syringe 50 includes a barrel 510 and a ram 520. The syringe clip 60 is fixedly provided on the first surface 110. The syringe clip 60 is configured to clamp and fix the syringe 50. The push handle seat 210 is provided with a syringe snap 211. The syringe snap 211 is configured for snapping the syringe 50 on the push handle seat 210.

One end of the connecting rod 220 extends into the through hole 121 and is connected with the driving device 20. The other end of the connecting rod 220 extends out of the through hole 121 and is connected with the push handle seat 210. One end of the infusion tube 530 is connected with the barrel 510. The other end of the infusion tube 530 is connected with a puncture needle 540. The first pressure sensor 710 is fixedly provided on the push handle seat 210. The alarm device 90 is provided inside the housing 10 and electrically connected with the processor 30.

Specifically, the display device 40 is configured to be foldable and can be covered on the first surface 110, so that the syringe 50 can be arranged in the accommodation space, which reduces an overall size of the syringe pump and makes it more convenient for medical staff to use and carry.

Figure 3:
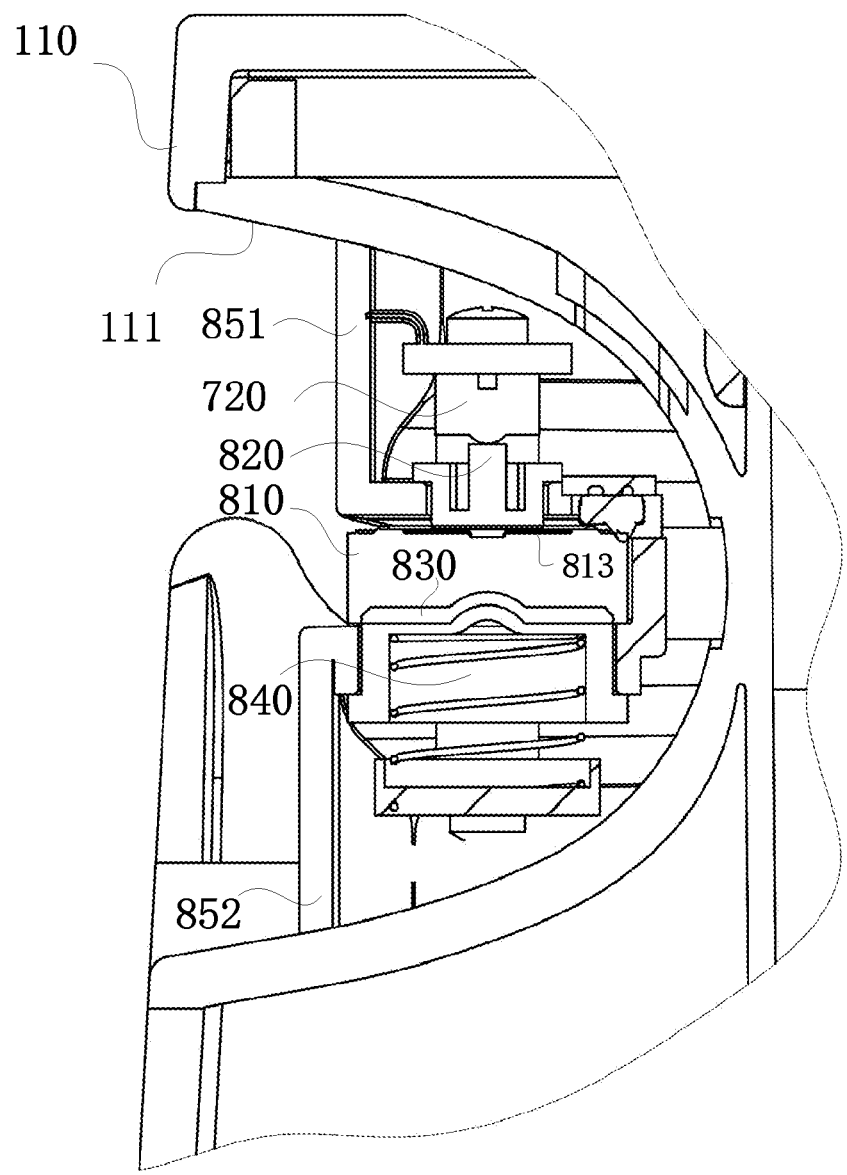
FIG. 3 is a structural schematic diagram of a pressure detection module in a syringe pump according to an embodiment of the present disclosure.
Figure 4:
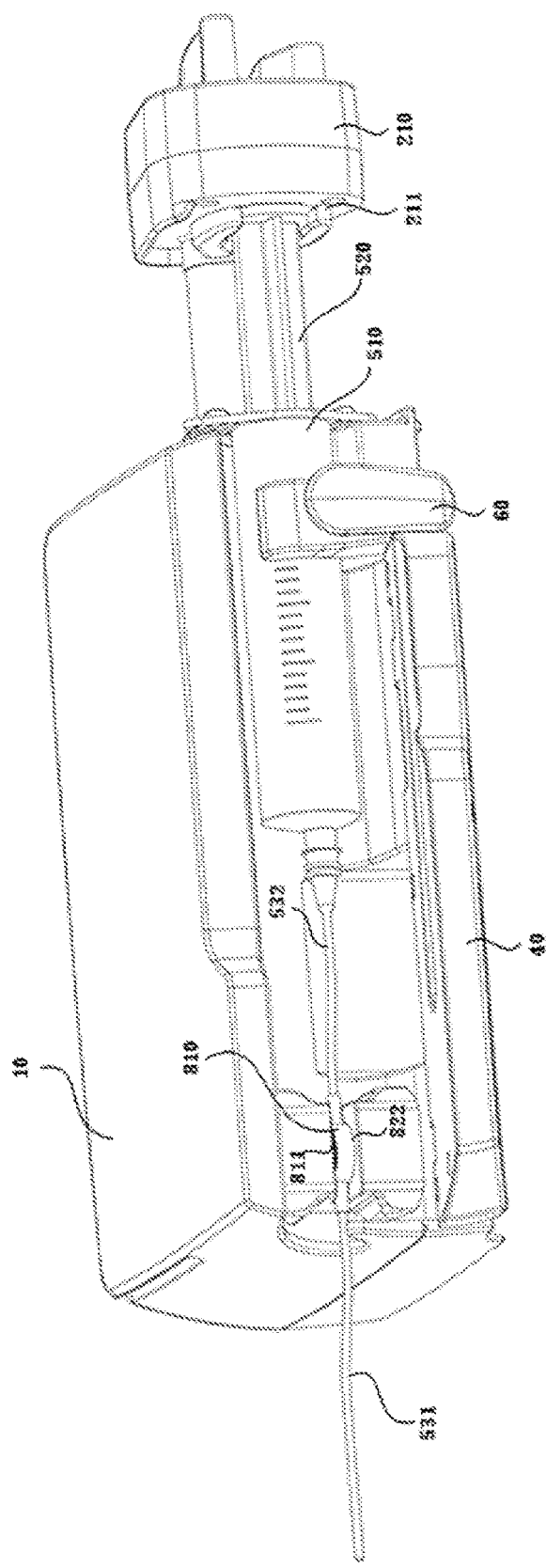
FIG. 4 is a structural schematic diagram of a syringe pump with a pressure detection module according to an embodiment of the present disclosure.

As shown in FIGS. 3 and 4, in an embodiment of the present disclosure, the first surface 110 is provided with a groove 111, and the infusion tube 530 includes a first tube 531 and a second tube 532. The syringe pump also includes a pressure detection module 80. The pressure detection module 80 is embedded in the groove 111. The pressure detection module 80 includes a membrane piece 810.

A flexible membrane 813 is provided on a first surface of the membrane piece 810. The flexible membrane 813 can be recessed in a direction close to a second surface of the membrane piece 810. One end of the first tube 531 is connected with the puncture needle 540, and the other end of the first tube is connected with the membrane piece 810. One end of the second tube 532 is connected with the membrane piece 810, and the other end of the second tube is connected with the barrel 510.

Specifically, the membrane piece 810 is a two-way consumable, and a front and back of the membrane piece 810 are connected with the first tube 531 and the second tube 532, respectively. The flexible membrane 813 is provided on the first surface 811 of the membrane piece 810, which can accurately reflect a pressure change in the infusion tube. Specifically, a depression, although subtle, makes a second pressure sensor 720 in a subsequent embodiment receive the pressure change in the infusion tube.

In this embodiment, when the puncture needle penetrates into the blood vessel of the subject, the pressure in the infusion tube affected by the blood pressure of the subject is acquired by the first pressure sensor and a pressure threshold is calculated according to the pressure in the infusion tube affected by the blood pressure of the subject, thus realizing the accurate and real-time calculation of the injection pressure that the subject can bear before injecting liquid medicine. A real-time detection of the pressure in the infusion tube during an injection process is realized, by acquiring the pressure of the first pressure sensor in real time during the injection process. By determining whether the pressure of the first pressure sensor is less than the pressure threshold and actively stopping the injection process when the pressure of the first pressure sensor is greater than or equal to the pressure threshold, it can be achieved to accurately determine whether the subject can bear an injection pressure, and to actively stop the injection when the pressure in the infusion tube exceeds a bearing limit of the subject, thus ensuring personal safety of the subject.

Continuing with reference to FIGS. 3 and 4, in an embodiment of the present disclosure, the pressure detection module 80 further includes a second pressure sensor 720. The second pressure sensor 720 is attached to the first surface of the membrane piece 811. The second pressure sensor 720 is configured to detect the pressure in the infusion tube.

Specifically, the second pressure sensor 720 is actually attached to the flexible membrane 813. During the injection process, the liquid medicine passes through the infusion tube 530, resulting in the pressure change. Sensitivity of the second pressure sensor 720 is high so that the pressure change in the infusion tube can be acquired through the depression of the flexible membrane 813.

Continuing with reference to FIGS. 3 and 4, in an embodiment of the present disclosure, the pressure detection module 80 further includes a pressure conducting block 820. The pressure detection module 80 is provided between the second pressure sensor 720 and the membrane piece 810. The pressure conducting block 820 is attached to the flexible membrane 813.

Specifically, the pressure conducting block 820 in this embodiment serves to increase contact area between the second pressure sensor 720 and the flexible membrane 813, so that the pressure in the infusion tube acquired by the second pressure sensor 720 is more accurate.

Continuing with reference to FIGS. 3 and 4, in an embodiment of the present disclosure, the pressure detection module 80 further includes a spring 840 and a pressure support block 830. The pressure support block 830 is arranged between the spring 840 and the membrane piece 810. The pressure support block 830 is attached to a second surface 812 of the membrane piece.

At least one bump is provided on a surface of the pressure support block 830. At least one pocket is provided on the second surface of the membrane piece 812. The bump and the pocket are arranged to be matched with each other, so that the pressure support block 830 and the membrane piece 810 are closely attached.

Specifically, the spring 840 and the pressure support block 830 both serve to support the membrane piece 810. Under action of the spring 840, the membrane piece can be prevented from being stressed from the subject, thereby preventing the membrane piece 810 from being pulled out.

As shown in FIG. 3, in order to save space, the pressure conducting block 820, the second pressure sensor 720, the spring 840 and the pressure support block 830 are all arranged in the groove 111 of the first surface 110. The pressure conducting block 820 and the second pressure sensor 720 are wrapped by an upper protective housing 851 to prevent the device from being damaged. The spring 840 and the pressure support block 830 are wrapped by a lower protective housing 852 to prevent the device from being damaged.

The membrane piece 810 is clamped between the upper protective housing 851 and the lower protective housing 852. All components of the above pressure detection module 80 are closely connected in the above manner, and a connection is firm and difficult to fall off.

Continuing with reference to FIGS. 3 and 4, in an embodiment of the present disclosure, the sensitivity of the second pressure sensor 720 is greater than that of the first pressure sensor 710.

Specifically, contents introduced in this embodiment has already been explained, so it is not repeated here.

The disclosure also provides a computer-readable storage medium.

In an embodiment of the present disclosure, the computer-readable storage medium includes a computer program. When the computer program is executed on a syringe pump, the syringe pump is caused to execute the control method of the syringe pump according to any one of the above embodiments.

The technical features of the above-mentioned embodiments can be combined in an arbitrary manner, and an execution sequence of steps of the method is not limited. For simplicity of description, not all of the possible combinations of the technical features in the embodiments described above are described, however, as long as there is no contradiction between these combinations of the technical features, the combinations should be considered as falling within the scope of this specification.

The above-mentioned embodiments only represent several embodiments of this disclosure, and their descriptions are specific and detailed, but they should not be understood as limiting the scope of this disclosure as such. It should be noted that, several modifications and improvements can be made for those of ordinary skill in the field without departing from the concept of this disclosure, which belong to the protection scope of this disclosure. Therefore, the protection scope of this disclosure shall be subjected to the appended claims.

What is claimed is:

1. A syringe pump comprising:
   a housing, a first surface of which is concave and a second surface of which is provided with a through hole;
   a push handle seat provided with a syringe snap which is configured for snapping the syringe on the push handle seat;
   a driving device provided inside the housing to drive the push handle seat to move;
   a processor provided inside the housing to send control orders to drive the push handle seat to move;
   a display device movably connected with the first surface, the display device being configured to be foldable so that when the display device is folded in a direction close to the first surface, the display device can be covered on the first surface to form an accommodation space with the first surface;
   a syringe provided in the accommodation space, the syringe including a barrel and a ram;
   a syringe clip fixedly provided on the first surface for clamping and fixing the syringe;
   a connecting rod, one end of which extends into the through hole is connected with the driving device, and an other end of which extends out of the through hole and is connected with the push handle seat;

an infusion tube, one end of which is connected with the barrel and an other end of which is connected with a puncture needle;

a first pressure sensor fixedly provided on the push handle seat;

a second pressure sensor attached to a first surface of a membrane piece for detecting a pressure in the infusion tube; and an alarm device provided inside the housing and electrically connected with the processor;

wherein the processor is implemented for acquiring a pressure value of the first pressure sensor in real time, determining whether the pressure value of the first pressure sensor is smaller than a first pressure threshold; and controlling the driving device to stop driving the push handle seat to move if the pressure value of the first pressure sensor is greater than or equal to the first pressure threshold;

the processor is further implemented for acquiring a pressure value of the second pressure sensor if the pressure value of the first pressure sensor has been determined to be smaller than the first pressure threshold, determining whether the pressure value of the second pressure sensor is smaller than a second pressure threshold; and controlling the driving device to stop driving the push handle seat to move if the pressure value of the second pressure sensor is greater than or equal to the second pressure threshold.

2. The syringe pump according to claim 1, wherein the first surface is provided with a groove, the infusion tube comprises a first tube and a second tube, and the syringe pump further comprises:

a pressure detection module embedded in the groove; the pressure detection module comprising:

the membrane piece further comprising a second surface of the membrane piece, a flexible membrane being provided on the first surface of the membrane piece and the flexible membrane being recessed in a direction close to the second surface of the membrane piece; and one end of the first tube being connected with the puncture needle, and the other end of the first tube being connected with the membrane piece; and one end of the second tube being connected with the membrane piece, and the other end of the second tube being connected with the barrel.

3. The syringe pump according to claim 2, wherein the pressure detection module further comprises:

a pressure conducting block provided between the second pressure sensor and the membrane piece and attached to the flexible membrane.

4. The syringe pump according to claim 3, wherein the pressure detection module further comprises a spring and a pressure support block; wherein the pressure support block is arranged between the spring and the membrane piece and is attached to the second surface of the membrane piece; and at least one bump is provided on a surface of the pressure support block, and at least one pocket is provided on the second surface of the membrane piece, the at least one bump and the at least one pocket being arranged to be matched with each other, so that the pressure support block and the membrane piece are closely attached.

5. The syringe pump according to claim 4, wherein sensitivity of the second pressure sensor is greater than that of the first pressure sensor.

* * * * *